United States Patent [19]

Tracy et al.

[11] Patent Number: 4,885,371

[45] Date of Patent: Dec. 5, 1989

[54] PROCESS FOR THE PREPARATION OF PURIFIED N-ALKYL LACTAMS

[75] Inventors: David J. Tracy, Lincoln Park; Mohamed M. Hashem, Wayne, both of N.J.

[73] Assignee: GAF Chemicals Corporation, Wayne, N.J.

[21] Appl. No.: 369,966

[22] Filed: Jun. 22, 1989

[51] Int. Cl.$^4$ .......................................... C07D 207/267
[52] U.S. Cl. .................................... 548/554; 548/543
[58] Field of Search ................................ 548/554, 543

[56] References Cited

U.S. PATENT DOCUMENTS 3,140,294  7/1964  Kolyer ............................... 548/554

FOREIGN PATENT DOCUMENTS 976939  12/1964  United Kingdom ................ 548/554

*Primary Examiner*—David B. Springer
*Attorney, Agent, or Firm*—Marilyn J. Maue; Joshua J. Ward

[57] ABSTRACT

The present invention relates to a process for the selective preparation of an N-alkyl lactam having minimal coloration by reacting the corresponding lactone with an alkyl amine in the presence of a catalytic amount of an ammonium, alkali metal or alkaline earth metal borohydride.

11 Claims, No Drawings

PROCESS FOR THE PREPARATION OF PURIFIED N-ALKYL LACTAMS

BACKGROUND OF THE INVENTION

N-alkyl lactams are useful in a great number of applications which include solubilizers and thickening agents for cosmetics, anti-drip and odor masking agents for paints, varnishes and the like, and anti-microbial additives for various medicinal and cleansing formulations. These compounds also have good solvating and complexing properties and are used as coatings or finishing agents to provide gloss and to improve the texture of treated substrates. A major drawback to the wide application of these chemicals is their coloration which ranges from a tawny yellow to brown, so that for many purposes, primarily in the cosmetic, paint and varnish arts their use has been restricted.

Accordingly, it is an object of this invention to provide substantially colorless N-alkyl lactam products.

Another object of this invention is to provide a decolorized product which can be produced by economical and commercially feasible methods.

Still another object is to provide a N-alkyl lactam product having extended uses and which can be employed in formulations at higher concentrations without causing discoloration.

These and other objects of the invention will become apparent from the following description and disclosure.

THE INVENTION

According to this invention a primary amine containing from 1 to 20 carbon atoms is reacted with butyrolactone optionally substituted on a carbon atom with lower alkyl in a mole ratio of from about 0.75:1 to about 1.25:1 in the presence of a catalytic amount of an ammonium, alkali metal or alkaline earth metal borohydride at a temperature of from about 225° C. to about 325° C. in a closed system. In the above reaction, the alkali metal borohydride is generally maintained at a concentration of between about 25 and about 1,000 ppm with respect to amine. The hydride can be admixed with the reactor feed or can be introduced after the reaction is initiated. If desired, the product of the reaction can be contacted under milder conditions with the borohydride salt as a final processing step.

The above reaction is generally carried out in the absence of solvent; although the components can be diluted up to about 50% with any inert organic solvent, such as a high boiling aliphatic hydrocarbon, e.g. ISOPAR V (sold by Exxon Chemical Corp.), if desired.

The above condensation reaction is allowed to take place over a period of from about 1 to about 20 hours, preferably from about 4 to about 8 hours, after which the reaction is completed. The resulting liquid product is then cooled, solvent if used is removed, and the resulting colorless liquid is then recovered as the product of the process.

Preferred conditions for the present process include a mole ratio of primary alkyl amine to lactone of between about 1:1.05 to 1:1.3, a concentration of borohydride salt with respect to amine of between about 100 and about 200 ppm and a reaction temperature of from about 250° C. to about 300° C.

The lactones of the present process are those having the formula

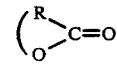

wherein R is alkylene having 3 carbon atoms which can be substituted with lower alkyl.

Examples of lactone reactants include butyrolactone, 3-methyl butyrolactone, 4-butyl-butyrolactone, and others known in the art. Examples of suitable primary amines include methyl amine, ethyl amine, butyl amine, coco amine, tallow amine, octyl amine, 2-ethyl hexylamine, decyl amine, dodecyl amine, tetradecyl amine, tolyl amine, etc. and mixtures thereof. Preferred amines are aliphatic amines having from 8 to 20 carbon atoms.

The borohydride moiety of the borohydride salt component employed in the present process can be derived from a gas, such as diborane ($B_2H_6$), a liquid such as pentaborane ($B_5H_9$) or a crystalline substance such as decaborane ($B_{10}H_{14}$) up to $B_{20}H_{26}$. Examples of suitable borohydride salts include ammonium borate ($NH_4HB_4O_7 \cdot 3H_2O$), sodium borohydride ($NaBH_4$), potassium borohydride ($KBH_4$), etc. Also, mixtures of the borohydride salts can be employed, if desired. Alternatively, the borohydride salt can be formed in situ from the metal hydroxide or ammonium hydroxide and pyroboric acid.

It appears that the metal borohydride salt component in the above reaction reduces color forming impurities, some of which may enter the system with the amine reactant. Such impurities can include metal salts such as chromium, copper and or cobalt salt residues from the catalyst employed in the preparation of the amine reactant. It is postulated that the borohydride can additionally form a complex with metal impurities and can act as a scavenger for metal oxides; thus preventing the formation of color bodies. The borohydride salt has a unique decolorizing effect which is not shared by common decolorizing agents such as peroxides, polyclar, carbon black and others. In addition, the borohydride minimizes the generation of amine oxidation products some of which are known to have toxic properties.

Having generally described the invention reference is now had to the accompanying examples which set forth preferred embodiments and comparative data but which are not to be construed as limiting to the scope of the invention which is more broadly set forth above and in the appended claims.

EXAMPLE 1

Into a 5 gallon autoclave is charged 7,752 grams of cocoamine and 3,595 grams of butyrolactone. The autoclave is sealed and heated to 275° C. and held for 8 hours at this temperature during which time 400 psig is generated by the reaction. The reactor is cooled and the resulting liquid, N-coco-pyrrolidone is discharged and analyzed by gas chromatography. The product is obtained in 97% yield and has a color value of 5 on a scale of 1 to 10, based on the Hellige Comparator Wheel-Varnish Color Disk 620C-40 (Institute of Paint and Varnish Research).

EXAMPLE 2

Into a 1-liter autoclave is charged 436.6 grams of the cocoamine reactant used in Example 1, 202.0 grams of butyrolactone and 0.06 grams of sodium borohydride. The autoclave is heated to 275° C. and held at that temperature for 8 hours during which time 400 psig. is generated by the reaction. The reactor is then cooled and the liquid N-coco-pyrrolidone product is discharged and analyzed by gas chromatography. The product is obtained in 97% yield and registered a color value of 3 on the Hellige Comparator Wheel.

EXAMPLE 3

Example 2 was repeated except that 150 ppm of sodium borohydride is employed based on amine. The yield of product was 97% and the liquid registered a color value of 2 on the Hellige Comparator Wheel.

EXAMPLE 4

Example 2 was repeated except that dodecyl amine was substituted for cocoamine. The yield and color of the liquid N-dodecylpyrrolidone product was comparable to that of Example 2.

EXAMPLE 5

Example 2 was repeated except that tallow amine was substituted for cocoamine. The yield and color of the liquid N-tallow pyrrolidone product was comparable to that of Example 2.

EXAMPLE 6

Example 2 is repeated except that polyclar is substituted for sodium borohydride. The resulting liquid product was recovered in 97% yield; however, the liquid registered 5 in the color test.

When Example 2 is repeated using other decolorants as by the post addition of hydrogen peroxide, polyclar, activated carbon, sodium hypochlorite, sodium hypophosphite or sodium chlorite, all failed to improve the color of the product.

What is claimed is:

1. The process which comprises reacting a primary amine containing from 1 to 20 carbon atoms with a butyrolactone optionally substituted on a carbon atom with lower alkyl in a mole ratio of from about 0.75:1 to about 1.25:1 in the presence of a catalytic amount of a borohydride salt selected from the group of an ammonium, alkali metal and alkaline earth metal salt of a borohydride or mixtures thereof to produce the corresponding lactam product.

2. The process of claim 1 wherein said borohydride salt is an alkali metal salt.

3. The process of claim 2 wherein said borohydride salt is $NaBH_4$.

4. The process of claim 1 wherein said primary amine contains from 8 to 20 carbon atoms and is an aliphatic amine.

5. The process of claim 4 wherein said amine is cocoamine, the lactone is butyrolactone and the lactam is N-coco-pyrrolidone.

6. The process of claim 4 wherein said amine is tallow amine, the lactone is butyrolactone and the lactam is N-tallow-pyrrolidone.

7. The process of claim 1 wherein the concentration of borohydride salt with respect to lactone is between about 25 and about 1,000 ppm.

8. The process of claim 7 wherein the ratio of primary amine to lactone is between about 1:1.05 and about 1:1.3, and the borohydride salt is introduced with reactant feed in a concentration of between about 100 and about 200 ppm with respect to amine.

9. The process of claim 1 wherein the lactam product is contacted with between about 25 and about 1,000 ppm of said borohydride salt at ambient temperature and pressure.

10. The product of the process of claim 1 having a Hellige Comparator Wheel color value less than 5.

11. The N-alkyl-pyrrolidone product of claim 1 having a Hellige Comparator Wheel color value of 3 or less.

* * * * *